US009697327B2

(12) United States Patent
McMillen et al.

(10) Patent No.: US 9,697,327 B2
(45) Date of Patent: *Jul. 4, 2017

(54) DYNAMIC GENOME REFERENCE GENERATION FOR IMPROVED NGS ACCURACY AND REPRODUCIBILITY

(71) Applicant: Edico Genome Corporation, La Jolla, CA (US)

(72) Inventors: Robert McMillen, La Jolla, CA (US); Michael Ruehle, La Jolla, CA (US); John Cooper Roddey, La Jolla, CA (US)

(73) Assignee: Edico Genome Corporation, La Jolla, CA (US)

(*) Notice: Subject to any disclaimer, the term of this patent is extended or adjusted under 35 U.S.C. 154(b) by 92 days.

This patent is subject to a terminal disclaimer.

(21) Appl. No.: 14/630,571

(22) Filed: Feb. 24, 2015

(65) Prior Publication Data

US 2015/0339437 A1 Nov. 26, 2015

Related U.S. Application Data

(60) Provisional application No. 61/943,870, filed on Feb. 24, 2014.

(51) Int. Cl.
*G06G 7/58* (2006.01)
*G06F 19/22* (2011.01)

(52) U.S. Cl.
CPC .................................. *G06F 19/22* (2013.01)

(58) Field of Classification Search
CPC ........................................................ G06F 19/22
USPC .......................................................... 703/11
See application file for complete search history.

(56) References Cited

U.S. PATENT DOCUMENTS

| 6,112,288 | A  | 8/2000  | Ullner             |
| 6,681,186 | B1 | 1/2004  | Denisov et al.     |
| 7,948,015 | B2 | 5/2011  | Rothberg et al.    |
| 8,209,130 | B1 | 6/2012  | Kennedy et al.     |
| 8,217,433 | B1 | 7/2012  | Fife               |
| 8,445,945 | B2 | 5/2013  | Rothberg et al.    |
| 8,524,487 | B2 | 9/2013  | Fife               |
| 8,558,288 | B2 | 10/2013 | Rothberg et al.    |
| 8,594,951 | B2 | 11/2013 | Homer              |
| 8,936,763 | B2 | 1/2015  | Rothberg et al.    |
| 9,014,989 | B2 | 4/2015  | McMillen et al.    |
| 2003/0033279 | A1 | 2/2003 | Gibson et al.     |
| 2005/0131649 | A1 | 6/2005 | Larsen et al.     |
| 2007/0088510 | A1 | 4/2007 | Li et al.         |
| 2008/0086274 | A1 | 4/2008 | Chamberlain et al.|
| 2008/0250016 | A1 | 10/2008| Farrar            |
| 2009/0125248 | A1 | 5/2009 | Shams et al.      |
| 2011/0004413 | A1 | 1/2011 | Carnevali et al.  |
| 2012/0001615 | A1 | 1/2012 | Levine            |
| 2012/0089339 | A1 | 4/2012 | Ganeshalingam et al.|
| 2012/0109849 | A1 | 5/2012 | Chamberlain et al.|
| 2013/0091121 | A1 | 4/2013 | Galinsky          |
| 2013/0245958 | A1 | 9/2013 | Forster et al.    |
| 2013/0311106 | A1 | 11/2013| White et al.      |
| 2013/0316331 | A1 | 11/2013| Isakov et al.     |
| 2013/0324417 | A1 | 12/2013| Kennedy et al.    |
| 2013/0332081 | A1 | 12/2013| Reese et al.      |
| 2013/0338934 | A1 | 12/2013| Asadi et al.      |
| 2014/0033125 | A1 | 1/2014 | Meral             |
| 2014/0114582 | A1 | 4/2014 | Mittelman et al.  |
| 2014/0121116 | A1 | 5/2014 | Richards et al.   |
| 2014/0236490 | A1 | 8/2014 | McMillen et al.   |
| 2014/0309944 | A1 | 10/2014| McMillen et al.   |
| 2014/0371109 | A1 | 12/2014| McMillen et al.   |
| 2014/0371110 | A1 | 12/2014| Van Rooyen et al. |

FOREIGN PATENT DOCUMENTS

| WO | 2013128371   | 9/2013  |
| WO | 2014060305   | 4/2014  |
| WO | 2014074246   | 5/2014  |
| WO | 2014113736 A1| 7/2014  |
| WO | 2014186604 A1| 11/2014 |
| WO | 2015123600 A1| 8/2015  |

OTHER PUBLICATIONS

Al Junid et al. "Development of Novel Data Compression Technique for Accelerate DNA Sequence Alignment Based on Smith-Waterman Algorithm." Highlighted. University Technology MARA (UiTM). 2009 Third UKSim European Symposium on Computer Modeling and Simulation. pp. 181-186.

Al Junid et al. "Optimization of DNA Sequences Data for Accelerate DNA Sequences Alignment on FPGA." University Technology MARA (UiTM). 2010 Fourth Asia International Conference on Mathematical/Analytical Modelling and Computer Simulation. pp. 231-236.

Edward Fernandez et al. PowerPoint presentation on "Multithreaded FPGA Acceleration of DNA Sequence Mapping." UC Riverside, Department of Computer Science and Engineering Jacquard Computer. 2012.

Guo, Xinyu et al., "A Systolic Array-Based FPGA Parallel Architecture for the BLAST Algorithm", IRSN Bioinformatics, 2012, 12 pg, vol. 2012, Article ID 195658.

Herbordt, Martin et al., "Single Pass Streaming BLAS on FPGAs", NIH Public Access Author Manuscript, Nov. 2007, 25 pgs, Parallel Comput.

Herbordt, Martin, et al., "Single Pass, BLAST-like, Approximate String Matching of FPGAs", Boston University, 2006, 19 pgs, Boston.

Jacob, Arpith et al., "FPGA-Accelerated seed generation in Mercury BLASTP", Washington University in St. Louis, BECS Technology Inc. (2007). 10 pgs.

Edward Fernandez et al. PowerPoint presentation on "Multithreaded FPGA Acceleration of DNA Sequence Mapping." UC Riverside, Department of Computer Science and Engineering Jacquard Computer. 2012.

Guo, Xinyu et al., "A Systolic Array-Based FPGA Parallel Architecture for the BLAST Algorithm", IRSN Bioinformatics, 2012, 12 pg, vol. 2012, Article ID 195658.

Herbordt, Martin et al., "Single Pass Streaming BLAS on FPGAs", NIH Public Access Author Manuscript, Nov. 2007, 25 pgs, Parallel Comput.

Herbordt, Martin, et al., "Single Pass, BLAST-like, Approximate String Matching of FPGAs", Boston University, 2006, 19 pgs, Boston.

Jacob, Arpith et al., "FPGA-Accelerated seed generation in Mercury BLASTP", Washington University in St. Louis, BECS Technology Inc. (2007). 10 pgs.

*Primary Examiner* — Jerry Lin (74) *Attorney, Agent, or Firm* — Mintz Levin Cohn Ferris Glovsky and Popeo, P.C.

(57) ABSTRACT

A "dynamic" reference is presented that utilizes population level information to improve reference-based alignment to detect novel, deleterious, or functional variants in clinical sequencing applications. An automatically updated database of known genetic variants is provided to a memory connected with an integrated circuit configured for genetic sequence data with the dynamic reference and reference variants.

4 Claims, 5 Drawing Sheets

(56) References Cited

OTHER PUBLICATIONS

Kasap, Server et al, "Design and Implementation of an FPGA-based Core for Gapped BLAST Sequence Alignment with the Two-Hit Method", Engineering Letters, 16:3 EL_16_3_25, Aug. 20, 2012, 10 pgs, Scotland, UK (2008).
Lancaster Joseph, "Design and Evaluation of a BLAST Ungapped Extension Accelerator, Master's Thesis", Washington University, Jan. 1, 2006, 79 pgs, Report No. WUCSE-20016-21, 2006 St. Louis.
Lancaster Joseph, et al. "Acceleration of Ungapped Extension in Mercury BLAST", MSP-7th Workshop on Media and Streaming Processors, Nov. 2005, 9 pgs.
Muriki, Krishna et al., "RC-BLAST: Towards a Portable, Cost-Effective Open Source Hardware Implementation" Supported in part by NSF Grant EIA-9985986, (2005). 8 pgs.
Sotiriades Euripides, et al. "FPGA based Architecture for DNA Sequence Comparison and Database Search", University of Crete, 2006, 8 pgs, Crete, Greece.
Sotiriades Euripides, et al., "Some Initial Results on Hardware BLAST acceleration with a Reconfigurable Architecture", University of Crete, 2006, 8 pgs, Crete, Greece.
TimeLogic Division, Active Motif Inc., "Accelerated BLAST Performance with Tera-Blast: a comparison of FPGA versus GPU and CPU Blast implementations", Technical Note, May 2013, 5 pages, Version 1.0.

DRAGEN Wavefront Processor Available on a PCIe Card for NGS Sequencers

FIG. 1

DRAGEN Architecture for Mapping/Aligning/Sorting/Dedup

SEQUENCE LISTING

```
<160> NUMBER OF SEQ ID NOS: 1

<210> SEQ ID NO 1
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 1
accgattgca gtcaaagtcc tgtgtcacgt gtacttggcg cacaaacctg tg          52
```

DYNAMIC GENOME REFERENCE GENERATION FOR IMPROVED NGS ACCURACY AND REPRODUCIBILITY

CROSS-REFERENCE TO RELATED APPLICATION

This application claims priority under 35. U.S.C. §119(e) to U.S. Provisional Application Ser. No. 61/943,870, filed Feb. 24, 2014, entitled "Dynamic Genome Reference Generation for Improved NGS Accuracy and Reproducibility", referenced in this paragraph and incorporated by reference in its entirety.

REFERENCE TO A "SEQUENCE LISTING," A TABLE, OR A COMPUTER PROGRAM LISTING APPENDIX SUBMITTED AS AN ASCII FILE

The Sequence Listing written in file 49927-502001US ST25, created Mar. 20, 2017, 636 bytes, machine format IBM-PC, MS Windows operating system, is hereby incorporated by reference.

TECHNICAL FIELD

The subject matter described herein relates to genomics, and more particularly to dynamic genome reference generation for improved next generation sequencing (NGS) accuracy and reproducibility

BACKGROUND

As DNA sequencing costs have plummeted over the last few years, raw data generated by sequencing has increased exponentially, measuring petabytes of data, making analyses and transfer of all this data difficult. These large amounts of data produce a critical bottleneck in the DNA sequencing workflow that has previously only been addressable by throwing increasing numbers of ever more powerful CPU cores at the problem. However, since the data being produced by sequencing already far outpaces Moore's Law, this solution has very limited sustainability.

The hugely parallel approach of NGS requires a human reference genome to be used to reconstruct the patient's genome from the raw read data. The human reference genome has become essential for clinical applications, and is used to identify alleles for risk, protection, or treatment-specific response in human disease. Yet, the current reference genome, GRCh38, being based on a limited number of samples, neither adequately represents the full range of human diversity, nor is complete. Further, the existing approach followed by the GRC and the genomics industry to construct a "static" reference genome introduces biases in standard bioinformatic pipelines used to detect the unique complement of variants in an individual's genome. An elegant, cost effective bioinformatics pipeline solution to perform the analysis of the sequenced data rapidly, accurately and in a consistent, reproducible way based on a truly population-wide reference is the final frontier to commoditize sequencing.

SUMMARY

In one aspect, a Next Generation Sequencing (NGS) bioinformatics ASIC (Application Specific Integrated Circuit) is disclosed. A "dynamic" reference is introduced that utilizes population level information to improve reference-based alignment to detect novel, deleterious, or functional variants in clinical sequencing applications. To generate the dynamic reference, an automatically-updated database of known genetic variants (SNPs, indels, CNVs, etc., archived at e.g. dbSNP, DGVa, dbVar) is built and provided, and augments a standard reference genome with the variants, to be processed by the NGS ASIC.

Implementations of the current subject matter can include, but are not limited to, systems and methods consistent including one or more features are described as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

To address these and potentially other issues with currently available solutions, methods, systems, articles of manufacture, and the like consistent with one or more implementations of the current subject matter can, among other possible advantages, provide a Next Generation Sequencing (NGS) bioinformatics ASIC (Application Specific Integrated Circuit). It enables the computational time required for the NGS data analysis pipeline to be radically reduced from many hours down to only a few minutes.

This dramatic speed improvement addresses the "static" reference issue in a way that has not been previously possible. A "dynamic" genome reference is provided that utilizes population level information to improve reference-based alignment to detect novel, deleterious, or functional variants in clinical sequencing applications. To generate the dynamic reference, an automatically updated database of known genetic variants (SNPs, indels (insertions/deletions), CNVs, etc., archived at e.g. dbSNP, DGVa, dbVar) is also provided, and augments a Wavefront Processor to utilize this data to enhance the standard reference genome with these variants.

Figure 1:
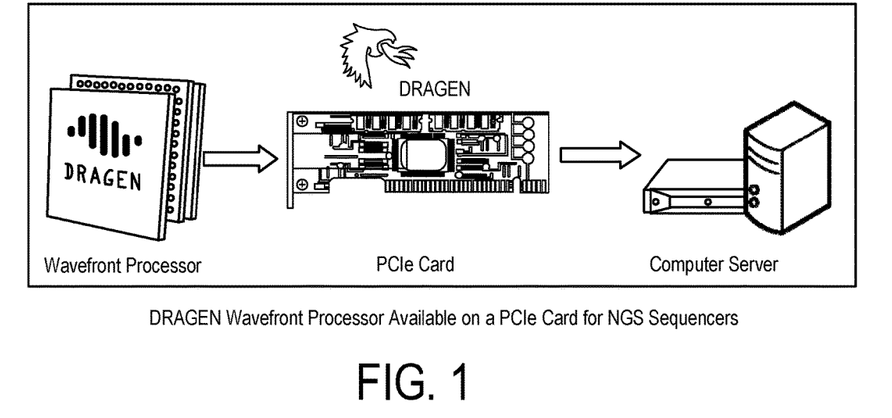
FIG. 1 shows a Wavefront Processor on a PCIe card for NGS sequencers.
Figure 2:
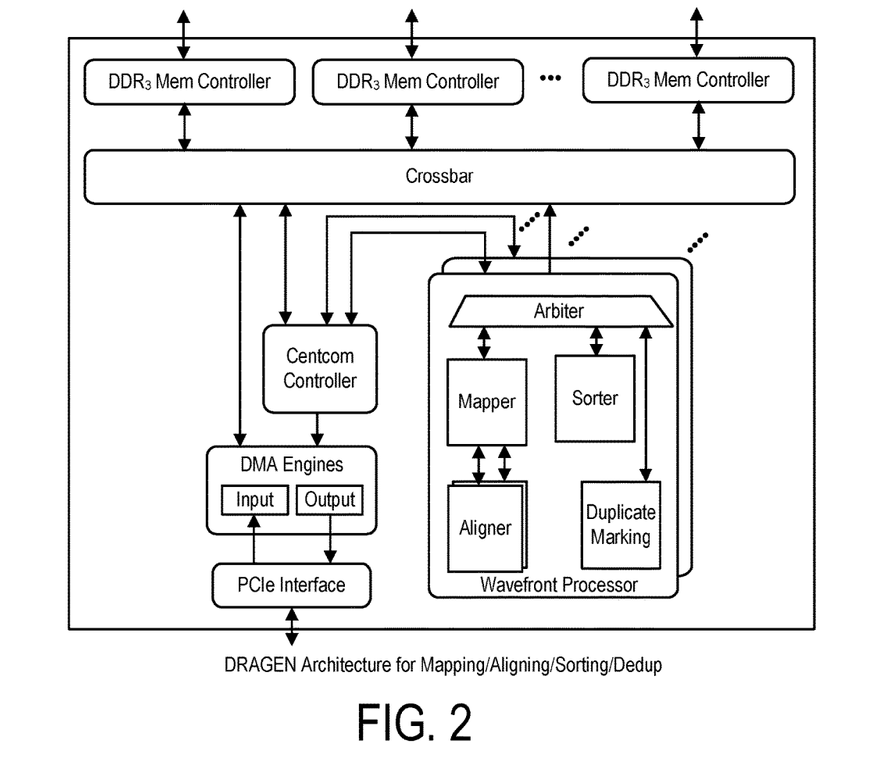
FIG. 2 shows an architecture for mapping, aligning, sorting and de-duplication of genomic sequence data.
Figure 3:
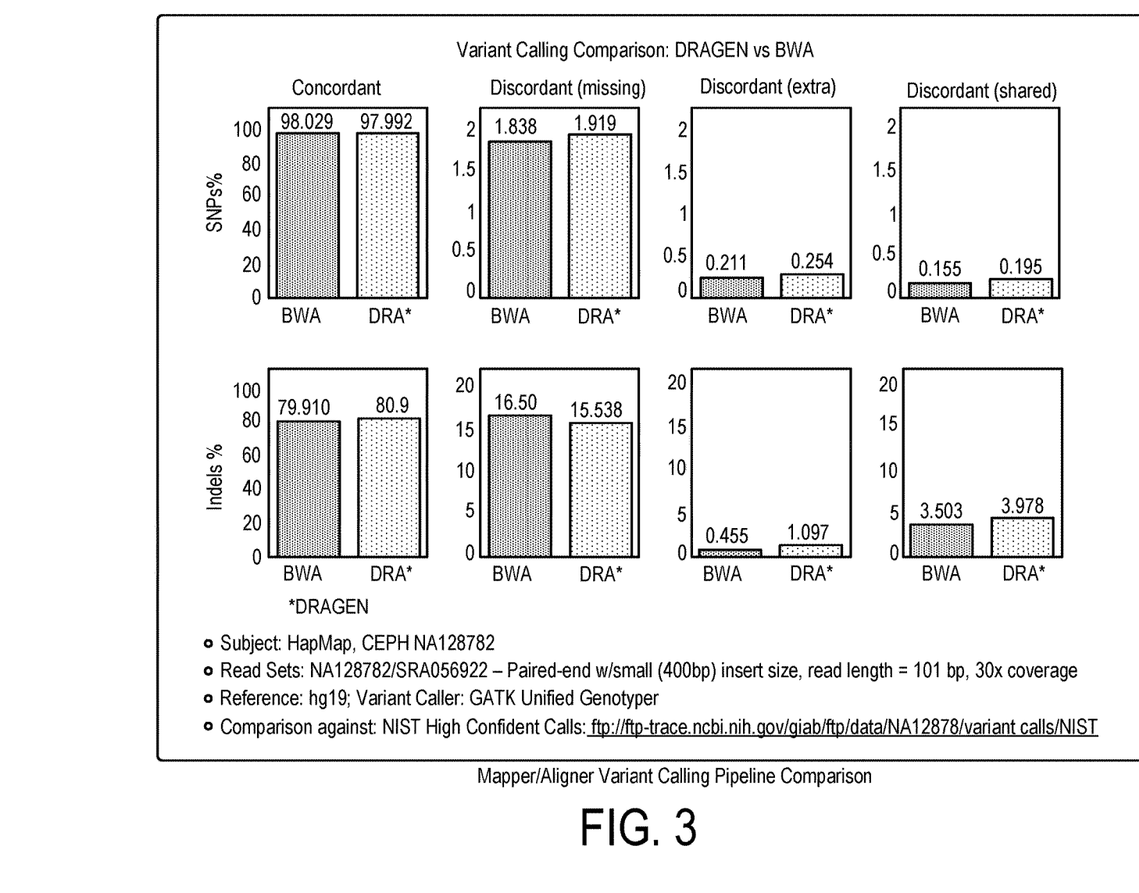
FIG. 3 illustrates a mapper/aligner variant calling pipeline comparison.

The Wavefront Processor is shown in FIGS. 1 and 2. The Wavefront Processor enables the computational time required for the whole genome sequencing (WGS) data analysis pipeline to be radically reduced from many hours down to only a few minutes at unprecedented quality (FIG. 3). The Wavefront Processor includes a configurable hardware architecture (FPGA) to speed up read mapping, alignment, sorting, and duplicate marking. Additionally, a number of modular extensions are provided to address the need to account for human diversity.

Figure 4:
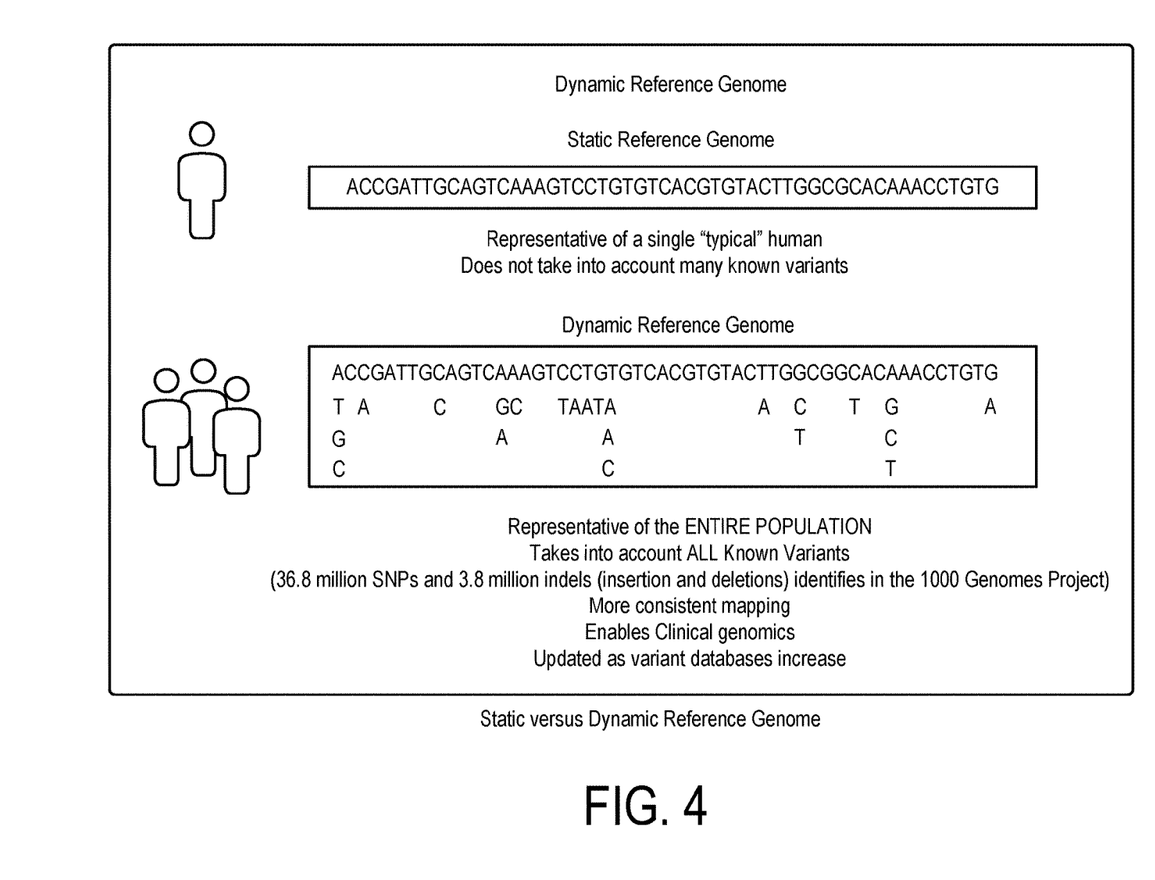
FIG. 4 illustrates static versus dynamic reference genomes. Sequence legend: accgattgca gtcaaagtcc tgtgtcacgt gtacttggcg cacaaacctg tg (SEQ ID NO:1).

The reference genome has been a guiding principle for the development of a vast array of computational tools and forms the foundation for databases and bioinformatics algorithms that are used to define target regions for re-sequencing, perform genome wide association studies, or measure inter-species conservation. The human reference genome has become essential for clinical applications, and is used to identify alleles for risk, protection, or treatment-specific response in human disease. Yet, the current reference genome, GRCh38, being based on a limited number of samples, neither adequately represents the full range of human diversity, nor is complete. Further, the existing approach followed by the GRC and the genomics industry to construct a "static" reference genome introduces biases in standard bioinformatic pipelines used to detect the unique complement of variants in an individual's genome, as shown in FIG. 4.

Figure 5:
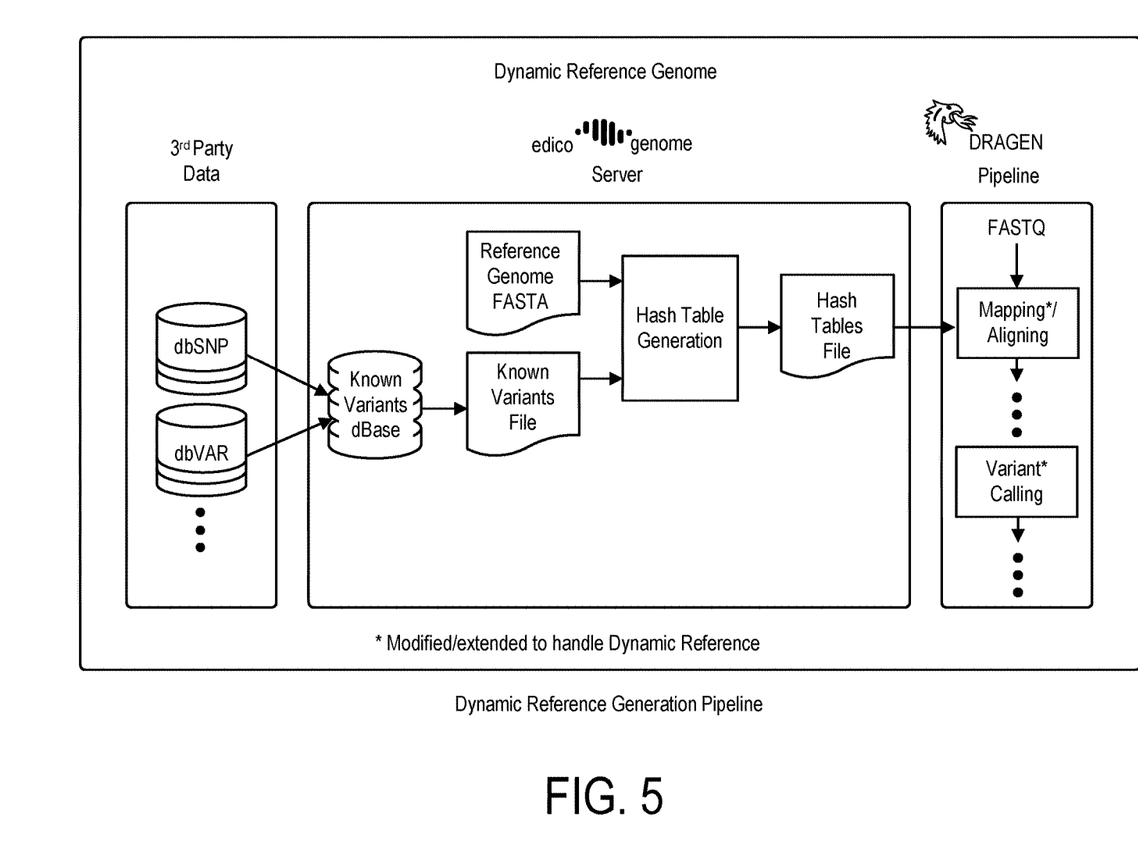
FIG. 5 shows a dynamic reference generation pipeline.

To address this problem, the "dynamic" reference is introduced (FIG. 4) that utilizes population level information to improve reference-based alignment to detect novel, deleterious, or functional variants in clinical sequencing applications. To generate the dynamic reference an automatically updated database of known genetic variants (SNPs, indels, CNVs, etc., archived at e.g. dbSNP, DGVa, dbVar) is built, and augments a standard reference genome with the variants in a manner analogous to conventional methodologies, as shown in FIG. 5.

Figure 6:
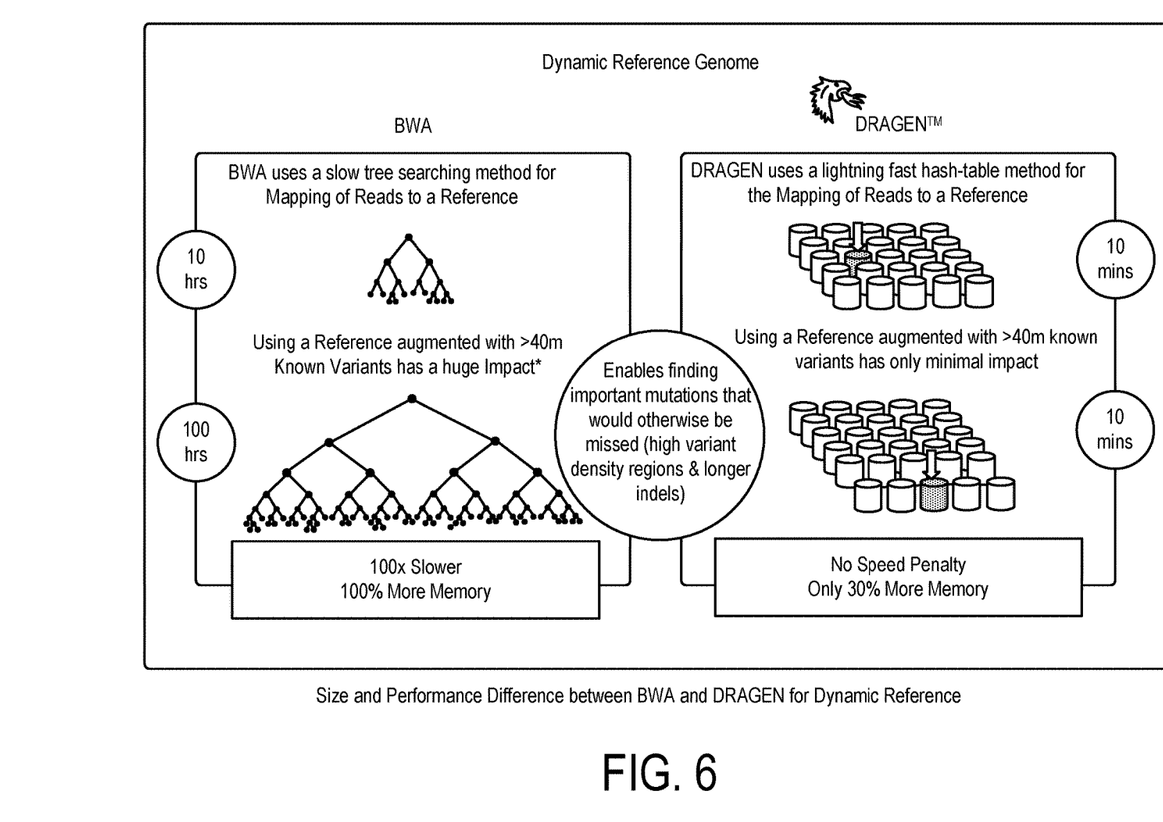
FIG. 6 illustrates size and performance differences between BWA and the Wavefront Processor with dynamic reference.

A Burrows-Wheeler transform (BWT) based aligner has been developed that maps reads to a dynamic reference genome. Importantly, alignment accuracy can be markedly improved in SNP-dense regions and regions with long indels that are often problematic for successful alignment of short reads. For BWT-based aligners (e.g. BWA), as the number of variants included in a dynamic reference increases, memory usage and run times increase. As illustrated in FIG. 6, augmentation can double the amount of memory required and cause the algorithm 100 times longer to run. In some implementations consistent with the current disclosure, the memory footprint can be increased approximately 30% with more variants, especially indels. However, for a hash-based algorithm, run times are expected to remain relatively constant. Furthermore, as more variants are identified and incorporated into the dynamic reference in the future, the alignment accuracy of the Wavefront Processor will continue to improve with little change in run times.

To support a dynamic reference, reads aligning to alternate sequences that overlap primary sequences (chromosomes) in most cases must be re-aligned to the correct primary sequence with properly adjusted FLAG, RNAME, POS, MAPQ, and CIGAR SAM fields. The CIGAR strings for a read aligning to an indel alternate sequence must be translated for proper alignment with the corresponding primary sequence. If such a read maps to a rare indel sequence, its MAPQ value may be penalized to decrease the chance of a false positive variant call. This penalty can be determined empirically with ground truth variant call data.

Aligning reads longer than ~1000 bases is impractical from a memory standpoint if indel alternate sequences are padded with sufficient bases to ensure alignment of full reads. For aligning very long reads, a compact representation of indel alternate sequences (without base padding) will be developed. In essence, each indel sequence must be stitched across the primary sequence region that it overlaps so that bases flanking the indel are coded just once in the dynamic reference.

Together with already-proven Mapping/Aligning/Sorting technology, as described in U.S. patent application Ser. No. 14/158,758, filed Jan. 17, 2014, entitled BIOINFORMATICS SYSTEMS, APPARATUSES, AND METHODS EXECUTED ON AN INTEGRATED CIRCUIT PROCESSING PLATFORM, the contents of which are incorporated by reference herein for all purposes, the dynamic reference genome and extensions to the Pipeline Processor that are described herein have a large impact on the quality of analysis results that can be achieved. Not only are rate and quality of variant identification increased from sequence data that is generated by a variety of next generation sequencing technologies, but accuracy of interpretive analysis of variant data is improved to provide novel e-diagnostics for the future, and deeper understanding of disease and its application in a clinical context.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable or hardwired system or computing system may interface with client computers and server computers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, Programmable Logic Devices (PLDs), and gate arrays, used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT), a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system for executing a sequence analysis pipeline on genetic sequence data, the system comprising:
   an electronic data source that provides digital signals representing a plurality of reads of genomic data, each of the plurality of reads of genomic data comprising a sequence of nucleotides;
   a first memory storing one or more genetic reference sequences and an index of the one or more genetic reference sequences;
   a second memory storing a database of reference variants; and
   an integrated circuit formed of a set of hardwired digital logic circuits that are interconnected by a plurality of physical electrical interconnects, one or more of the plurality of physical electrical interconnects comprising an input to the integrated circuit connected with the electronic data source for receiving the plurality of reads of genomic data, one or more of the plurality of physical electrical interconnects further comprising a memory interface for the integrated circuit to access the memory, the hardwired digital logic circuits being arranged as a set of processing engines, each processing engine being formed of a subset of the hardwired digital logic circuits to perform one or more steps in the sequence analysis pipeline on the plurality of reads of genomic data, each subset of the hardwired digital logic circuits being in a wired configuration to perform the one or more steps in the sequence analysis pipeline, the set of processing engines comprising:
      a mapping module in the wired configuration to access, according to at least some of the sequence of nucleotides in a read of the plurality of reads, the index of the one or more genetic reference sequences from the memory via the memory interface to map the read to one or more segments of the one or more genetic reference sequences or reference variants based on the index, wherein the index of the one or more genetic reference sequences further comprises a hash table, and wherein the mapping module applies a hash function to the at least some of the sequence of nucleotides to access the hash table of the index; and an alignment module in the wired configuration to access the one or more genetic reference sequences from the memory via the memory interface to align the read to one or more positions in the one or more segments of the one or more genetic reference sequences from the mapping module; and one or more of the plurality of physical electrical interconnects comprising an output from the integrated circuit for communicating result data from the mapping module and/or the alignment module.

2. The system in accordance with claim 1, wherein the integrated circuit further comprises a master controller to establish the wired configuration for each subset of the hardwired digital logic circuits to perform the one or more steps in the sequence analysis pipeline.

3. The system in accordance with claim 1, wherein the integrated circuit comprises a field programmable gate array (FPGA) of the hardwired digital logic circuits.

4. The system in accordance with claim 1, wherein the wired configuration is established upon manufacture of the integrated circuit and is non-volatile.

* * * * *